United States Patent [19]

Montgieux

[11] Patent Number: 4,696,307
[45] Date of Patent: Sep. 29, 1987

[54] DEVICE FOR CONTINUOUSLY DETECTING THE BREATHING RHYTHM, IN PARTICULAR WITH A VIEW TO PREVENTING THE SUDDEN DEATH OF AN INFANT DUE TO CESSATION OF BREATHING DURING SLEEP

[76] Inventor: Francois F. Montgieux, 15, rue Palapharnerie, 84000 Avignon, France

[21] Appl. No.: 774,445

[22] Filed: Sep. 10, 1985

[30] Foreign Application Priority Data

Sep. 11, 1984 [FR] France ................. 84 13915

[51] Int. Cl.⁴ ............................................. A61B 5/10
[52] U.S. Cl. .................................... 128/721; 128/782; 340/573
[58] Field of Search .................. 128/716, 721–723, 128/774, 782, 644, 640, 802–803, 687, 689; 340/573, 575

[56] References Cited

U.S. PATENT DOCUMENTS

| Re. 32,180 | 6/1986 | Lewiner et al. | 128/782 |
| 4,409,983 | 10/1983 | Albert | 128/689 X |
| 4,426,884 | 1/1984 | Polchaninoff | 128/774 X |
| 4,509,527 | 4/1985 | Fraden | 128/774 X |
| 4,576,179 | 3/1986 | Manus et al. | 128/644 X |

Primary Examiner—Lee S. Cohen
Assistant Examiner—Angela D. Sykes
Attorney, Agent, or Firm—William A. Drucker

[57] ABSTRACT

A device for continuously detecting the breathing rhythm, especially with a view to preventing the sudden death of an infant owing to cessation of breathing during sleep including a self-contained device for detecting and signalling the breathing rhythm of a child and equipped with a detector for sensing an abnormal respiratory pause and generating an alarm signal when this pause exceeds a predetermined period, this device being housed inside a small box designed to be laid directly on the body of the child. Fasteners are provided for fixing the box onto the body of the child in such a way as to keep the application face of the box against the skin of the child.

7 Claims, 4 Drawing Figures

DEVICE FOR CONTINUOUSLY DETECTING THE BREATHING RHYTHM, IN PARTICULAR WITH A VIEW TO PREVENTING THE SUDDEN DEATH OF AN INFANT DUE TO CESSATION OF BREATHING DURING SLEEP

BACKGROUND OF THE INVENTION

1. Field of the invention

The present invention concerns a device for continuously detecting breathing rhythm, in particular, but not exclusively, with a view to preventing the sudden death of an infant due to apnea or stoppage of breathing during sleep.

It is widely recognized that apnea in an infant is currently the prime cause of death amongst children aged less than twelve months. This syndrome is still unexplained and there currently exists no effective means to prevent such deaths.

The only possible action that can be taken, especially as regards the prevention of recurrences, consists of continuous cardiorespiratory surveillance of the child whilst it is asleep so as to be able to detect if breathing has stopped, and, where this continues, to proceed with elementary first-aid measures such as jlts, artificial respiration or even,in certain cases, external cardiac massage. Owing to the fact that this syndrome can occur after only several minutes of sleep, it is necessary, if one desires to exclude any possibility of accident, to keep the infant under twenty-four surveillance.

Consequently, as regards the current state of the technique, for such surveillance to be fully effective, it needs to be provided in a hospital centre using quite expensive equipment requiring the constant presence of a medical assistant. Now, the time the infant spends in the hospital centre is often insufficient to eliminate every risk, all the more so because the decision to stop continuous surveillance is usually difficult to take owing to the lack of formal criteria for eliminating risks.

2. Description of the prior art

With the aim of overcoming these drawbacks, devices have already been proposed enabling breathing surveillance of an infant to be carried out in the home. These devices usually appear in the form of an electronic box or "monitor" connected by linkage, e.g. pneumatic or electronic, to one or more detectors intended to be attached to the body of the infant or in close proximity to the latter.

However, a first drawback of these devices, apart from the fact that they are still expensive, is that the links between the monitor and the child make them awkward to use, especially when dressing, undressing or moving the infant. In addition, the fact of the infant moving may result in the connections being pulled and consequently the sensors being moved or damaged, thus rendering them ineffective which could set off false alarms.

A second drawback is that the sensors and possibly their links to the electronic box must be regularly changed and this makes the device more expensive to use.

A third drawback originates from the fact that, with a view to permitting surveillance, these devices usually produce light impulses and/or sound impulses (bips) in synchronism with the child's breathing rhythm. As a result, even in the case where they include means allowing an alarm signal to be generated (generally a sound signal) indicating absence of breathing exceeding a predetermined period, they require the continuous presence of someone in the immediate proximity of the device.

SUMMARY OF THE INVENTION

The invention thus aims to eliminate all these drawbacks.

With such aim in mind, it offers a device of the type which includes a device for detecting and signalling the breathing rhythm of the child supplied with means enabling an abnormal breathing pause to be discovered and an alarm signal to be generated when this pause exceeds a predetermined period, this device being particularly characterized in that:

(a) the detection and signalling device is self-contained and is housed inside a small box comprising an application wall whose outer face is designed to be kept in contact with the skin of the child in a suitable preselected place, the said wall comprising at least one mobile detection zone responding to movements of the skin generated by the breathing process of the child;

(b) this detection and signalling device includes a transducer sensitive to movements of the detection zone;

(c) the box is equipped with fasteners to be connected to the body of the child and which are able to keep the said outer face of the application wal and, in particular, that of the detection zone, against the skin of the child.

The invention is not limited to a special type of transducer, provided the latter allows for transformation, into an electrical signal which can be used by the self-contained detection and/or signalling device, of the movements and/or pressure variations (thoratic and/or abdominal movements) produced on the skin at the place in question (e.g. close to the navel) during the respiratory cycle.

It should be mentioned that the detection devices act in combination with the box fastening means on the body of the child. Indeed, apart from their fastening function, these fastenings help, by means of the box, to provide the transducer with a position and/or a reference pressure which is essential for obtaining a significant response. In addition, the inertia of the whole box can also contribute to the acquisition of these reference parameters. Another advantage is that these fastening means could consist of an adhesive provided on the periphery of the application face of the box, such adhesive being designed to act directly on the child's skin or on an elastic or inextensible belt designed to encircle the child's body.

Moreover, the detection and signalling device, similar to known devices, can include means enabling light and/or sound pulses to be produced with each of the breathing cycles, as well as a sound alarm in the event of a prolonged stoppage of breathing, by means of the signalling devices provided inside the box.

However, in order to avoid the previously mentioned drawbacks concerning these signalling devices which are increased owing to the fact that the box is for the most part covered by the child's clothes, the invention provides in addition, to be used separately or in combination:

(a) a device for waking or resuscitating the child and which is capable, for example, of introducing electrodes through which current discharges are produced, and/or, (b) a transmitter (e.g. high frequency) placed inside the box and connected to at least one portable receiver carried by the person monitoring the child.

These two devices are controlled in response to the transmission of the above-mentioned alarm signal, possibly after a preselected interval of time.

In addition, the detection and signalling device may include means for:

(a) preselecting the time interval chosen between the stoppage of breathing and the transmission of the alarm signal (e.g. from five seconds to forty seconds per step of five seconds); and/or (b) preselecting the time interval chosen between the stoppage of breathing and the triggering of the device for waking the child (from twenty to sixty seconds per step of five seconds); and/or (c) inhibiting the sound signal transmitted on each breathing cycle of the child; and/or (d) automatically discharging (stoppage/setting) the sound alarm and/or the device for waking the child following renewed breathing; and/or (e) inhibiting the device for waking the child; and/or (f) the counting and display on demand of the number of respiratory pauses greater than a preselected time interval with the possibility of resetting the counter; and/or (g) inspecting the state of the battery used with the sound alarm for monitoring wear and tear of the latter; and/or (h) ensuring the proper electronic functioning by an independent electronic circuit with alarm in the event of malfunction.

BRIEF DESCRIPTION OF THE DRAWINGS

A method for realizing the invention shall now be described, by way of example by no means restrictive, with reference to the annexed drawings in which.

DESCRIPTION OF THE PREFERRED EMBODIMENT

Figure 1:
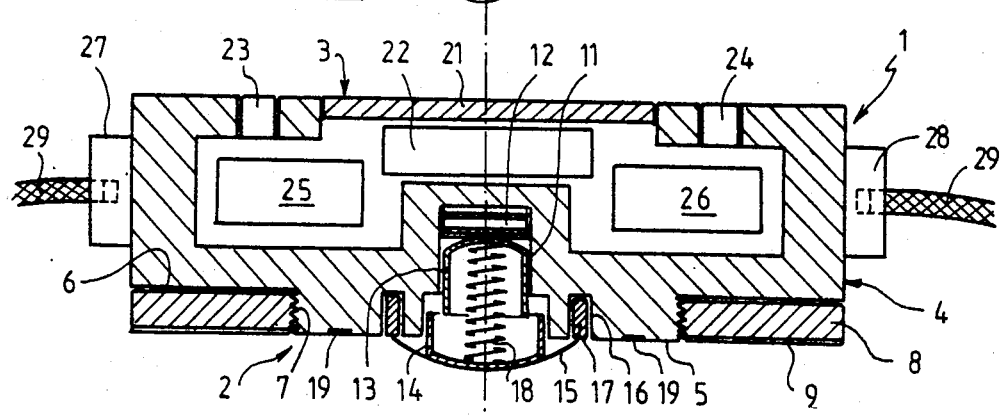
FIG. 1 is a diagrammatic axial section of a device according to the invention.

As represented on FIG. 1, the device for the continuous detection of the breathing rhythm of a child includes first of all a cylindrical box 1 being slightly larger than a watch case (several cm in diameter). Generally speaking, the shape of this box 1 and the choice of the material used are selected so that the box 1 can remain continuously on the child without the child being harmed in any way (irritation, pain, etc . . . ).

This box 1 in particular includes an application face 2, a display face 3 opposite the application face 2 and a cylindrical lateral wall 4.

The application face 2 of the box 1 comprises a circular central zone 5 connected to a peripheral zone in the shape of a ring 6 situated standing back by a shoulder 7 fitted with a thread. On this thread can be screwed a ring 8 whose lower face, which appears in the surface plane of the central zone after screwing, carries an adhesive lining 9.

At the centre of the zone 5, a coaxial cylindrical recess is provided inside which a detector is mounted comprising:

(a) a displacement transducer 12 housed at the bottom of the recess, (b) a first thruster 13 slidingly mounted inside the receiver 11 and coming to rest on the displacement transducer 12, (c) a second thruster 14 slidingly mounted inside the receiver 11 and kept in position by a flexible diaphragm 15 tightly mounted on the central zone 5 of the fixing face 2 by means of a circular groove 16 into which the peripheral edge 17 of the diaphragm is fixed, and (d) a pressure spring 18 disposed between the two thrusters 13, 14.

On the central zone 5 are also provided one or more electrodes 19 through which it is possible to transmit to the child a current discharge for resuscitating (waking) him.

The upper face 3 of the box 1 includes a transparent window 21 in line with which are disposed an indicator 22, a light source 23 and a sound source 24.

Of course, the box can also include means such as interruption thrusters or sensitive keys allowing for the starting of the device and the various preselections and controls required for setting the parameters of the device and operating it. In addition, it includes means of access to one or more batteries 25 supplying the electronic circuit 26 contained inside the box.

This electronic circuit which is connected to the transducer 12, the indicator 22, the light and sound sources 23 and 24, the electrodes 19 and to the thrusters of control switches (not represented) includes all the elements necessary for the device to function. This circuit, which introduces means with which the electronician is familiar and possibly a microprocessor and high frequency transmitter, does not form the object of the invention and consequently shall not be described.

On the lateral wall 4 of the box 1 are provided, in two diametrically opposed positions, means 27, 28 for fastening an abdominal belt 29, possibly elastic.

Figure 2:
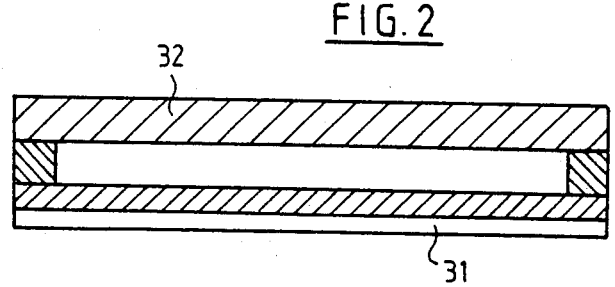
FIG. 2 is a diagrammatic representation of an electret displacement transducer used in the device shown in FIG. 1.

In this example, detection of breathing is based on the use, as regards the transducer 12, of an electret transmitter consisting of, as represented on FIG. 2, of a metallized electret 31 placed opposite an electrode 32 at a distance of several tenths of microns.

The electret 31 being charged, any movement of the latter in relation to the electrode 32 induces a current (between the electret and the electrode) provoked by an increase of positive or negative loads on the electrode 32. The loads induced on the electrode 32 are thus proportional to the amplitude of the displacement of the electret 31.

In this example, the invention uses this principle, but in this instance, the displacement of the electret 31 is not provoked by a sound vibration as in the case of a microphone, but by the unit consisting of the thrusters 13 and 14 and the spring 18.

Figure 3:
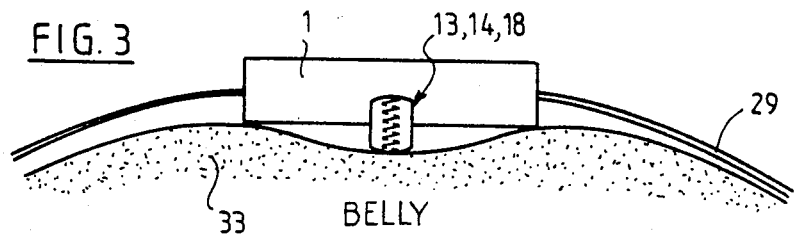
FIGS. 3 and 4 are diagrammatic views illustrating the principle of the displacement detector used in the device shown in FIG. 1.
Figure 4:
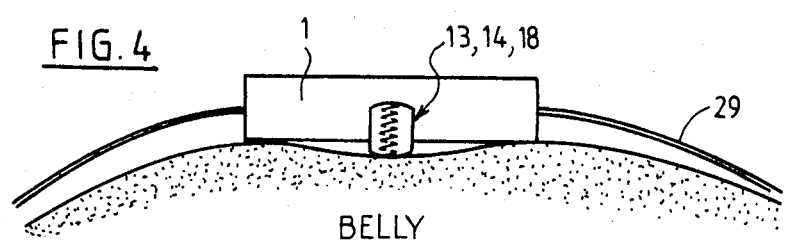

As illustrated by FIGS. 3 and 4, before breathing, the part of the belly 33 of the child and on which the box is placed 1 is relaxed and only exerts on the thrusters 13, 14/spring 18 unit a slight pressure (FIG. 3).

At the moment of breathing, the distension of the child's abdomen, partly absorbed by the elasticity of the abdominal belt 29, results in an axial displacement of the thruster.

This displacement is transmitted elastically to the thruster 13 by means of the compression spring 18 and, as a result, to the electret 31 which then delivers to the electronic circuit 26 a signal which is proportional to the amplitude of this displacement.

It should be mentioned that the use of the thrusters 13, 14/spring 18 unit for transmitting the strain exerted by the abdomen to the electret 31 is designed to avoid any risk of damage to the electret 31.

Of course, the invention is not limited to this transmission mode. Indeed, the stress of the electret 31 could, for example, be carried out by hydraulic transmission introducing a hydraulic fluid housed in the closed cavity defined by the diaphragm 15 and the recess 11, as well as by a piston driven by the hydraulic fluid and coming to rest on the electret transmitter.

Similarly, the electret transmitter could consist of any other pressure sensor and/or displacement transducer. In addition, it could consist of an ultrasound detection device, the hydraulic fluid then being replaced by a fluid ensuring direct transmission with possibly ultrasonic focussing on the detection device.

An important advantage of the devices according to the invention lies in the fact that they can operate without the addition of consumable equipment (electrode, contact gel, etc...), with the exception of the battery 25 which must be regularly renewed.

What is claimed is:

1. A device for the continuous detection of a child's breathing rhythm, in particular for preventing the sudden death of the child by the cessation of breathing during sleep, this device comprising a box having an application wall, said application wall comprising a rigid peripheral zone and a movable centreal zone adapted to follow movements produced on the child's skin by the child's breathing, said box housing a transducer which comprises a movable metallized electret, an electrode rigidly mounted in the box and placed opposite said electret and reducing means which are interposed between said movable zone and said electret and which transmit to said electret a fraction of the movements of said central zone, said electret being electrically charged and inducing on said electrode a current which is representative of said movements, said box being equipped with fasteners to be connected to the body of the child and which are adapted to keep said peripheral zone and said central zone against the skin of the child, said fasteners providing the transducer through said peripheral zone and said box with a reference position.

2. Device according to claim 1, wherein said reducing means consists in mechanical reducing means.

3. Device according to claim 1, characterized in that the said transducer and the said reducing means are housed inside a recess formed inside the application wall and reclosed by a flexible diaphragm which constitutes said central zone.

4. Device according to claim 3, characterized in that the said reducing means include a first mobile thruster coming to rest against the said transducer and a second thruster kept applied against the said diaphragm and in that a compression spring is disposed between the two thrusters.

5. Device according to claim 1, characterized in that the fasteners of the box consist of an adhesive provided on the periphery of the application wall of the box and designed to act directly on the child's skin.

6. Device according to claim 5, characterized in that the said adhesive is applied to a moving part coming to rest on the application wall of the box.

7. Device according to claim 6, characterized in that the said part consists of a ring screwed into a thread fitted on a shoulder of an outer face of the application wall of the box.

* * * * *